(12) United States Patent
Carter et al.

(10) Patent No.: US 8,343,486 B2
(45) Date of Patent: Jan. 1, 2013

(54) METHODS AND COMPOSITIONS FOR TOPICAL TREATMENT OF MEDICAL CONDITIONS INCLUDING WOUNDS AND INFLAMMATION

(75) Inventors: Stephen G. Carter, Andover, MA (US); Zhen Zhu, Tewksbury, MA (US); Kanu Patel, Londonderry, NH (US); Diane L. Kozwich, Nottingham, NH (US)

(73) Assignee: BioChemics, Inc., Danvers, MA (US)

( * ) Notice: Subject to any disclaimer, the term of this patent is extended or adjusted under 35 U.S.C. 154(b) by 765 days.

(21) Appl. No.: 12/358,078

(22) Filed: Jan. 22, 2009

(65) Prior Publication Data

US 2009/0214504 A1    Aug. 27, 2009

Related U.S. Application Data

(60) Provisional application No. 61/022,708, filed on Jan. 22, 2008.

(51) Int. Cl.
*A61K 38/43* (2006.01)

(52) U.S. Cl. ..................................................... 424/94.1

(58) Field of Classification Search .......................... None
See application file for complete search history.

(56) References Cited

U.S. PATENT DOCUMENTS

| 5,514,672 | A | 5/1996 | Bazzano | 514/168 |
| 5,652,261 | A | 7/1997 | Ismail | 514/458 |
| 6,284,797 | B1 | 9/2001 | Rhodes | 514/627 |
| 6,521,268 | B2 * | 2/2003 | You et al. | 424/725 |
| 2003/0018076 | A1 * | 1/2003 | Fossel | 514/565 |
| 2004/0097587 | A1 | 5/2004 | Arbiser | 514/559 |
| 2004/0265345 | A1 * | 12/2004 | Perricone | 424/401 |

FOREIGN PATENT DOCUMENTS

| WO | WO 2007/085902 A2 | 8/2007 |
| WO | WO 2007/085902 A3 | 8/2007 |

OTHER PUBLICATIONS

Paquette, D. et al. "Short-Contact Topical Tretinoin Therapy to Stimulate Granulation Tissue in Chronic Wounds," *Journal of the American Academy of Dermatology*, vol. 45, No. 3, Sep. 1, 2001, pp. 382-386.

Abdelmalek, M., et al. "Retinoids and Wound Healing," *Dermatologic Surgery, Inc.*, vol. 32, No. 10, Oct. 2006, pp. 1219-1230.

European Patent Office International Search Report and Written Opinion of the International Searching Authority, PCT/US2009/031731, dated Mar. 19, 2009.

* cited by examiner

*Primary Examiner* — Suzanne M Noakes
(74) *Attorney, Agent, or Firm* — Sunstein Kann Murphy & Timbers LLP

(57) ABSTRACT

A method for treating a patient suffering from a wound, ulcer, or inflammation includes providing a topical formulation comprising a carrier and a combination of active ingredients that includes at least one retinoid and at least one blood vessel dilator, and applying the topical formulation to the skin of the patient to cause healing, accelerated healing or prevention of the wound, ulcer or inflammation. Additional active ingredients may include a promoter of mitochondrial function or an antioxidant.

16 Claims, No Drawings

METHODS AND COMPOSITIONS FOR TOPICAL TREATMENT OF MEDICAL CONDITIONS INCLUDING WOUNDS AND INFLAMMATION

CROSS-REFERENCES TO RELATED APPLICATION

This patent application claims priority to Provisional U.S. Patent Application Ser. No. 61/022,708, filed Jan. 22, 2008, entitled "Methods and Compositions for Topical Treatment of Wounds and Inflammation" the entirety of which is hereby incorporated herein by reference.

TECHNICAL FIELD

The present invention relates to a pharmacological composition and method for treatment of medical conditions including wounds and inflammation.

BACKGROUND

Inflammation is the complex biological response of vascular tissues to pathogens, damaged cells, chemical signals or irritants. Inflammation may be thought of as an attempt by an organism to remove injurious stimuli and initiate tissue healing. Inflammation can be classified as either acute or chronic.

Acute inflammation is a short-term process characterized by swelling, redness, pain, heat, and loss of function caused by the increased movement of plasma and leukocytes from the blood into the injured tissues. Acute inflammation is initiated by the blood vessels adjacent to the injured tissue, which adapt to allow the exudation of plasma proteins and leukocytes into the surrounding tissue. The increased flow of fluid into the tissue causes the characteristic swelling associated with inflammation, and the increased blood flow to the area causes the reddened color and increased heat. The blood vessels are also altered to permit the extravasation of leukocytes through the endothelium and basement membrane constituting the blood vessel. Once in the tissue, the cells migrate along a chemotactic gradient to reach the site of injury, where they can attempt to remove the stimulus and repair the tissue. Several biochemical cascade systems, consisting of chemicals known as plasma-derived inflammatory mediators, act in parallel to propagate and mature the inflammatory response. These include the complement system, coagulation system and fibrinolysis system. Removal of the injurious stimuli causes down-regulation of the inflammatory response and concludes acute inflammation. Down regulation halts the recruitment of monocytes into the inflamed tissue, existing macrophages exit the tissue via lymphatics and wound healing begins. The causes of acute inflammation include

- Burns
- Chemical irritants
- Frostbite
- Toxins
- Infection by pathogens
- Necrosis
- Physical injury (blunt or penetrating)
- Immune reactions due to hypersensitivity
- Ionizing radiation
- Foreign bodies, including splinters and dirt The inflammatory response must be actively terminated to prevent unnecessary "bystander" damage to tissues, failure to do so results in prolonged inflammation and cellular destruction.

Prolonged inflammation, known as chronic inflammation, leads to a progressive shift in the type of cells which are present at the site of inflammation.

In chronically inflamed tissue the stimulus is persistent. As a result, recruitment of monocytes is maintained, existing macrophages are anchored in place, and macrophages proliferation is stimulated. Macrophage cells are powerful defensive agents but they release toxins including reactive oxygen species that are injurious to the organism's own tissues, leading to tissue destruction. Chronic inflammation can be caused by persistent acute inflammation, bacterial infection, prolonged exposure to a chemical agent, or autoimmune reactions to name a few causes.

Abnormalities associated with inflammation comprise a large, unrelated group of disorders which underlay a variety of human diseases including allergic reactions and some myopathies, cancer, atherosclerosis, ischemic heart disease, asthma, autoimmune diseases, chronic inflammation, chronic prostatitis, glomerulonephritis, hypersensitivities, inflammatory bowel diseases, pelvic inflammatory disease, reperfusion injury, rheumatoid arthritis, transplant rejection.

SUMMARY OF THE INVENTION

In accordance with an illustrative embodiment of the present invention, there is a method for treatment of a patient suffering from a wound, ulcer or inflammation. The method includes providing a topical formulation comprising a carrier and a combination of active ingredients that includes at least one retinoid and at least one blood vessel dilator, and applying the topical formulation to the skin of the patient to cause at least healing, accelerated healing or prevention of the wound, ulcer or inflammation.

The healing may be measured by a reduction in wound size or by a reduction in number of skin disruptions caused by neuropathy or myopathy. The formulation may be applied to the site of inflammation from physical injury, surgery, electric shock or burn to reduce the time required to heal the wound or to reduce the size of a resulting wound as compared to an untreated wound. The healing may cause a restoration of healthy skin. The wound, ulcer or inflammation may be one derived from cancer, arthritis, a digestive disorder, a myopathy, a neuropathy, a decubitous ulcer, a dermal ulcer associated with a colostomy, or an acute inflammation.

In a related embodiment, the method may include selecting a site of injury or inflammation and applying the formulation topically to a region proximate to the site.

In addition, the formulation may include at least one antioxidant, at least one promoter of mitochondrial function, or both. The combination may include at least one antioxidant selected from the group consisting of ascorbate, coenzyme Q10, and a tocopherol. The combination may include at least one promoter of mitochondrial function selected from the group consisting of L-carnitine and acetyl-L-carnitine. The retinoid include one or more of vitamin A (i.e., retinol), retinal, 9-cis-retinoic acid, tretinoin, isotretinoin, .etretinoin, or acitretin. The combination may also include a fatty acid ester such as palmitate or oleate. The at least one blood vessel dilator may be selected from the group consisting of methyl nicotinate, arginine, hexyl nicotinate, papaverine, tolazoline, acetylcholine, sodium nitroprusside, nitroglycerine, adensosine or a combination thereof. The formulation may be a stable emulsion. The formulation may include a stable emulsion of vitamin A and methyl nicotinate.

The concentration of vitamin A in the formulation may be at least 0.001% by weight, and the concentration of methyl nicotinate may be at least 0.01% by weight. The formulation maybe delivered using a patch.

In another embodiment, a formulation for topical administration may include a carrier and a combination of active ingredients consisting essentially of a retinoid and a blood vessel dilator.

In a yet another embodiment, a formulation for topical administration may include a carrier and a combination of active ingredients consisting essentially of a retinoid, a blood vessel dilator, and an antioxidant.

In a further embodiment, a formulation for topical administration may include a carrier and a combination of active ingredients consisting essentially of a retinoid, a blood vessel dilator, and a promoter of mitochondrial function.

In yet a further embodiment, a formulation for topical administration may include a carrier and a combination of active ingredients consisting essentially of a retinoid, a blood vessel dilator, an antioxidant and a promoter of mitochondrial function.

In connection with the aforementioned embodied formulations, the retinoid may be vitamin A, retinal, 9-cis-retinoic acid, tretinoin, isotretinoin, .etretinoin, or acitretin. Fatty acid esters such as palmitate or oleate may be included. The blood vessel dilator may be selected from the group consisting of methyl nicotinate, arginine, hexyl nicotinate, papaverine, tolazoline, acetylcholine, sodium nitroprusside, nitroglycerine, adensosine or a combination thereof. The antioxidant may be selected from the group consisting of ascorbate, coenzyme Q10, and a tocopherol, and the promoter of mitochondrial function may be selected from the group consisting of L-carnitine and acetyl-L-carnitine. Additionally, the active ingredients may be contained in a patch adapted for timed-release activity.

In another aspect of the invention, there is provided a formulation comprising a carrier and a combination of active ingredients that includes at least one retinoid and at least one blood vessel dilator for the treatment of a wound, ulcer or inflammation. The formulation is in one embodiment used for the promotion of healing or for acceleration of healing of a wound, ulcer or inflammation; or for the prevention of an ulcer or inflammation associated with a wound. The formulation may be for topical administration or subcutaneous administration.

In another aspect of the invention, there is provided the use of a formulation comprising a carrier and a combination of active ingredients that includes at least one retinoid and at least one blood vessel dilator in the preparation of a medicament for the treatment of a wound, ulcer or inflammation. In an embodiment, the use is for the promotion of healing or for acceleration of healing of a wound, ulcer or inflammation; or for the prevention of an ulcer or inflammation associated with a wound. The medicament may be provided for administration in topical or subcutaneous form.

DETAILED DESCRIPTION OF SPECIFIC EMBODIMENTS

Definitions. As used in this description and the accompanying claims, the following term shall have the meanings indicated, unless the context otherwise requires:

In the context of topical application, a "formulation" includes a delivery system such as a cream, lotion, gel, or a patch that is impregnated or otherwise carries or delivers an active ingredient or ingredients.

Embodiments of the present invention include formulations and the method of use of such formulations for the treatment of wounds or conditions associated with acute or chronic inflammation including acute inflammation cause by injury, surgery, burns or electric shock. Additionally, the formulations may be useful in the treatment of a decubitous ulcer, cancer, arthritis, digestive disorders, myopathies (including cardiac pathologies) and neuropathies, including inflammatory aspects of these disorders. The formulations may be applied topically or subcutaneously and comprise a mixture of components.

In an illustrative embodiment of the invention, a topical formulation includes a retinoid (such as vitamin A or analogue or derivative thereof) in addition to a blood vessel dilator. The blood vessel dilator may include, for example, methyl nicotinate, or a nitric oxide liberating agent such as L-arginine. The dilator may also include one or more of hexyl nicotinate, papaverine, tolazoline, acetylcholine, sodium nitroprusside, nitroglycerine, or adensosine, either alone, in combinations thereof, or in a combination with methyl nicotinate and/or L-arginine. The retinoid and dilator may be combined as part of a cream, lotion or gel for topical application.

The retinoid may include one or more of retinol, retinal, 9-cis-retinoic acid, tretinoin, isotretinoin, etretinoin, and acitretin. The retinol may be formulated with a fatty acid ester, e.g., palmitate and/or oleate.

Additional agents may be added to the formulation to increase therapeutic effectiveness in general or to enhance suitability for specific uses. These additional agents may include one or more of an antioxidant, and a promoter of mitochondrial function. The antioxidant may include, for example, ascorbate (e.g. as a sodium or calcium salt), tocopherol, co-enzyme Q10, or combinations thereof. The promoter of mitochondrial health may include, for example, L-carnitine, acetyl-L-carnitine, or combinations thereof. A lipophilic thiamine derivative such as benfotiamine may also be included. Analogues of derivates of these compounds may also be used.

The formulations may also have carrier substances, which may be inactive or may enhance the activity of the aforementioned active compounds. Examples of substances that may be used as carriers include caprylic acid, capric glyceride, soybean or other vegetable oils, vitamin E, TPGS, silicone, glyceryl stearate, glycerin, oleic acid, cetyl alcohol, olive oil, ethyl oleate, isopropyl myristate, propylparaben, allantoin, triethanolamine, acrylates (e.g., c10-30 alkyl acrylate copolymer), phenoxyethanol, hydroxypropyl methyl cellulose, and xantham gum. The formulation may include a stable emulsion of the active ingredients together with carriers.

In another embodiment, a method treats one or more of the aforementioned medical conditions. The method includes selecting a site of injury or inflammation and applying the formulation to a region proximal to the site. For example, the formulation may be applied one or more times per day. When absorbed through the stratum corneum the formulation may reduce inflammation in the microvascular and surrounding tissue at the site of application.

Additionally, the method may be used for systemic delivery of the active ingredients for treatment directed to remote sites including internal organs. Delivery may be aided by containing the active ingredients in a drug-delivery patch. Generally, the patch will deliver these ingredients in a timed-release manner; e.g., over a course of days.

Delivery of the formulation may also be accomplished via subcutaneous injection. For example, the formulation may be injected, in any of the various ways known in the art, at multiple sites along the periphery of a wound, inflamed area of skin, or other area in need of treatment.

A wound associated with cancer may be the result of the tumor growth compromising the skin and thus creating a wound or it may be associated with the chemotherapy and/or radiation therapy used to treat the cancer, which in turn results in a wound or an ulcer in the skin. The application of a formulation in accordance with one of the aforementioned embodiments of the invention to the cancer-associated wound may result in a reduction in the size of the wound and also a shortening of the time that the patient suffers from the presence of the wound or ulcer.

Neuropathy and Myopathy may result in a dermal wound or ulcer as a result of a cascade effect of physiologic disorders including loss of sensation to an area of the skin which in turn may result in the creation of a pressure-induced wound or other causes of dermal wounds and ulcers. The use of the topically applied formulation in accordance with one of the aforementioned embodiments of the invention may reduce the size of the wound once formed and if applied to the area of the insult, prior to the disruption of the skin surface it may result in the prevention of the disruption.

A wound associated with osteoarthritis or rheumatoid arthritis may be an open dermal wound or it may not compromise the surface of the skin. In either case the inflammation associated with the arthritic condition may be addressed with the use of the topically applied formulation in accordance with one of the aforementioned embodiments of the invention, with the result being a reduction in the size or surface area of the inflammation and wound as measured by either a reduction in the open wound area or a reduction in the size of the inflamed area as measured in part by a redness to the skin.

Certain digestive conditions may result in a colostomy apparatus being worn by the patient. A dermal ulcer or wound may develop at the site of the insertion of the device. The use of the topically applied formulation in accordance with one of the aforementioned embodiments of the invention may reduce the size of the wound resulting in the restoration of healthy skin tissue surrounding the device as well as shorten the time of the presence of the wound or ulcer.

Wounds and ulcers resulting from acute inflammation associated with physical actions such as accidental injury, surgery or electrical shocks and burns may be treated with topical formulations in accordance with one of the aforementioned embodiments of the invention with the result being the reduction in the time required to heal the wound and also a reduction in the size of the wound as opposed to an untreated wound.

Illustrative ranges of concentrations of active ingredients are given in the following table:

| Ingredient | Concentration range (% by weight) |
|---|---|
| Vitamin A | 0.001 to 5 |
| Vitamin C | 0.01 to 5 |
| Vitamin E | 0.01 to 10 |
| L-Arginine | 0.1 to 20 |
| Co-enzyme Q10 | 0.01 to 5 |
| L-Carnitine | 0.1 to 20 |

Wound Healing Preparation Example:

| | % by Weight |
|---|---|
| Part A | |
| Chemical Caprylic/Capric Glycerate | 2 |
| Olive Oil | 5 |
| Vitamin E | 0.5 |
| Vitamin A | 0.1 |
| Propylparaben | 0.1 |
| Dimethicone | 2 |
| Glyceryl Stearate | 5 |
| Part B | |
| Methylparaben | 0.2 |
| Glycerin | 2 |
| Xanthan Gum | 1 |
| L-Carntine | 2 |
| Arginine HCl | 0.5 |
| Water | 78.3 |
| Part C | |
| Phenoxyethanol | 0.7 |
| Coenzyme Q10 | 0.1 |
| Fragrance | 0.5 |
| Total | 100% |

Procedure:
1. Mix all the ingredients listed in Part A together, and heat to 70° C.
2. Weigh in the ingredients listed in Part B except Xanthan Gum.
   Turn on mixer at high speed, then sprinkle the Xanthan Gum in.
   Mix for 5 minutes, then heat to 70° C.
3. Add Part A into Part B at 70° C., mix for 10 mins. Then cool the mixture to 40° C.
4. Add ingredients in Part C into the mixture one by one at a temperature below 40° C. Mix for another 20 mins.

Usage of the Preparation:
Approximately 2 grams of the example material may be expressed into a gloved hand and applied with a gentle rubbing action to a decubitous ulcer and surrounding skin tissue until the material has been absorbed. Application may be repeated twice a day for 4 weeks.

The described embodiments of the invention are intended to be merely exemplary and numerous variations and modifications will be apparent to those skilled in the art. For example, other known retinoids, vasodilators, promoters of mitochondrial function, antioxidants, and excipients may be used. In addition, pharmaceutically acceptable salts of any of the disclosed compounds may be used. All such variations and modifications are intended to be within the scope of the present invention as defined in the appended claims. It is intended that the preambles of the claims that follow be given patentable weight.

What is claimed is:
1. A method for treatment of a patient suffering from a wound, ulcer, or inflammation the method comprising:
   providing a topical formulation comprising a carrier and a combination of active ingredients that includes at least one retinoid and at least one blood vessel dilator wherein the at least one retinoid of the formulation is vitamin A, and the at least one blood vessel dilator is methyl nicotinate, wherein the vitamin A and the methyl nicotinate are in a stable emulsion; and applying the topical formulation to the skin of a patient suffering from a wound, ulcer, or inflammation so as to at least cause healing or accelerated healing of the wound, ulcer or inflammation.

2. The method according to claim 1, wherein the concentration of vitamin A is at least 0.001% by weight, and the concentration of methyl nicotinate is at least 0.01% by weight.

3. A method for treatment of a patient suffering from a wound, ulcer, or inflammation the method comprising:

provinding a topical formulation comprising a carrier and a combination of active ingredients that includes at least one retinoid and at least two blood vessel dilators, the blood dilators consisting of methyl nicotinate and arginine; and applying the topical formulation to the skin of a patient suffering from a wound, ulcer, or inflammation so as to at least cause healing or accelerated healing of the wound, ulcer or inflammation.

4. The method according to claim 1 or 3, wherein the healing is measured by a reduction in the size of the wound.

5. The method according to claim 1 or 3, wherein the formulation is applied to the site of inflammation from physical injury, surgery, electric shock or burn so as to reduce the time required to heal the wound or reduce the size of a resulting wound as compared to an untreated wound.

6. The method according to claim 1 or 3, wherein the healing causes a restoration of healthy skin.

7. The method according to claim 1 or 3, wherein the wound, ulcer or inflammation is derived from one of cancer, arthritis, a digestive disorder, a myopathy, a neuropathy, a decubitous ulcer, a dermal ulcer associated with a colostomy, or an acute inflammation.

8. The method according to claim 1 or 3, further comprising selecting a site of injury or inflammation and applying the formulation topically to a region proximate to the site.

9. The method according to claim 1 or 3, wherein the combination also includes at least one antioxidant, at least one promoter of mitochondrial function, or both.

10. A method according to claim 9, wherein the combination includes at least one antioxidant selected from the group consisting of ascorbate, coenzyme Q10, and a tocopherol.

11. A method according to claim 9, wherein combination includes at least one promoter of mitochondrial function selected from the group consisting of L-carnitine and acetyl-L-carnitine.

12. The method according to claim 1 or 3, wherein the retinoid includes one or more of vitamin A, retinal, 9-cis-retinoic acid, tretinoin, isotretinoin, .etretinoin, or acitretin.

13. The method according to claim 12, further comprising a fatty-acid ester.

14. The method according to claim 13, wherein the fatty acid ester is palmitate or oleate.

15. The method according to claim 1 or 3, wherein the formulation is a stable emulsion.

16. The method according to claim 1 or 3, wherein the formulation is delivered using a patch.

* * * * *